United States Patent [19]

Weinberg

[11] Patent Number: 5,674,260
[45] Date of Patent: Oct. 7, 1997

[54] APPARATUS AND METHOD FOR MOUNTING AN ACTIVITY SENSOR OR OTHER COMPONENT WITHIN A PACEMAKER USING A CONTOURED HYBRID LID

[75] Inventor: Alvin H. Weinberg, Moorpark, Calif.

[73] Assignee: Pacesetter, Inc., Sylmar, Calif.

[21] Appl. No.: 604,633

[22] Filed: Feb. 23, 1996

[51] Int. Cl.[6] .................................... A61N 1/375
[52] U.S. Cl. ........................................ 607/36
[58] Field of Search ........................ 607/1, 2, 5, 9, 607/36, 116, 119

[56] References Cited

U.S. PATENT DOCUMENTS

| | | | |
|---|---|---|---|
| 4,254,775 | 3/1981 | Langer | 607/36 X |
| 4,614,194 | 9/1986 | Jones et al. | 607/9 |
| 5,144,946 | 9/1992 | Weinberg et al. | 607/2 |
| 5,314,458 | 5/1994 | Najafi et al. | 607/2 |
| 5,470,345 | 11/1995 | Hassler et al. | 607/36 |

*Primary Examiner*—Jeffrey R. Jastrzab

[57] ABSTRACT

A cardiac stimulation device contains an electronics package having a hybrid circuit structure enclosed by a contoured lid design. The contoured lid of the electronics package has a multi-level surface structure which conforms to a multi-level design of the hybrid circuit structure. Mounting the electronics package within a housing of the cardiac stimulation device creates an isolated region formed between the contoured lid of the electronics package and an interior surface of the housing. An activity sensor, or other component of the cardiac stimulation device, may be placed within the isolated region to reduce the overall size of the device.

15 Claims, 3 Drawing Sheets

APPARATUS AND METHOD FOR MOUNTING AN ACTIVITY SENSOR OR OTHER COMPONENT WITHIN A PACEMAKER USING A CONTOURED HYBRID LID

FIELD OF THE INVENTION

This invention relates generally to implantable pacemakers and the configuration of components within pacemakers. More particularly, this invention relates to methods and apparatus for integrating internal components of a pacemaker within confined regions of a pacemaker housing.

BACKGROUND OF THE INVENTION

As cardiac stimulation devices become more technologically complex, it has become challenging to reduce their overall size or even maintain their existing size. Reducing the size of a cardiac stimulation device benefits the patient who must carry the device, and it may also lead to an improved procedure for implanting the device. Accordingly, there are continuous efforts within the medical device industry to reduce the size of pacemakers, defibrillators and other implantable medical devices.

The size of a cardiac stimulation device is determined by the size and arrangement of its contents. Cardiac pacemakers, and other implantable cardiac stimulation devices, ordinarily contain an outer casing which houses a group of electronic components. The internal components of a pacemaker consist primarily of an electronics package, a battery, a motion detecting element, stimulus lead connectors, and circuitry for linking together these components. Efforts at reducing pacemaker size have focused both on miniaturizing the internal components and on uniquely configuring the internal components within the housing to minimize the space needed for such components. With respect to the electronics package of a pacemaker, these efforts have produced a complex hybrid circuit structure having miniature integrated circuits which are typically placed, or stacked, together.

With respect to the overall internal configuration of a pacemaker's components, many pacemakers and defibrillators alike contain a battery which is juxtaposed and coplanar with the electronics package. This leads to a slim pacemaker design which is dependent on the width of the battery and the electronics package.

Even with the many efforts at reducing pacemaker size, some internal electronic components of a pacemaker can be difficult to optimally locate within a housing in order to minimize pacemaker size. For example, a motion detecting element is used in most pacemakers to detect patient movement in order to regulate the proper pacing of the patient's heart. In many cases, the motion detecting element is mounted between the pacemaker housing and either the electronics package or the battery. In such a configuration, the overall width of a pacemaker unit is approximately the combined width of the battery, the motion detector and the housing. Thus, even with improvements in configuring pacemaker components, there is still inadequate room to house some components without increasing the overall size of a pacemaker.

Therefore, there is a need in the art for an improved pacemaker design which allows for the packaging of internal components in a smaller pacemaker housing.

SUMMARY OF THE INVENTION

In accordance with a preferred embodiment of the present invention, a cardiac stimulation device, such as a pacemaker, contains an electronics package having a contoured hybrid lid. The contoured lid covers the micro-electronic circuit structure mounted within the electronics package. The contoured lid has a multi-level outer surface which corresponds with the multi-layered micro-electronic circuit structure of the electronics package. The outer surface of the contoured lid and a pacemaker housing are fitted together to isolate a region within the housing which can accommodate additional circuit components of the pacemaker. As a result, components which before contributed to an increased size of a pacemaker are located within previously unused space.

In accordance with a preferred embodiment, a motion detecting element can be mounted within the isolated region created by the contoured lid of the electronics package. In the preferred embodiment, the resulting size of the pacemaker will have a width which is reduced by approximately the width of the motion detecting element. Thus, the overall external size of a pacemaker can be reduced by advantageously using a contoured lid design as disclosed herein to house internal pacemaker components.

BRIEF DESCRIPTION OF THE DRAWINGS

The above and other aspects, features and advantages of the present invention will be more apparent from the following particular descriptions thereof presented in conjunction with the following drawings wherein.

DETAILED DESCRIPTION OF THE PREFERRED EMBODIMENT

Figure 1:
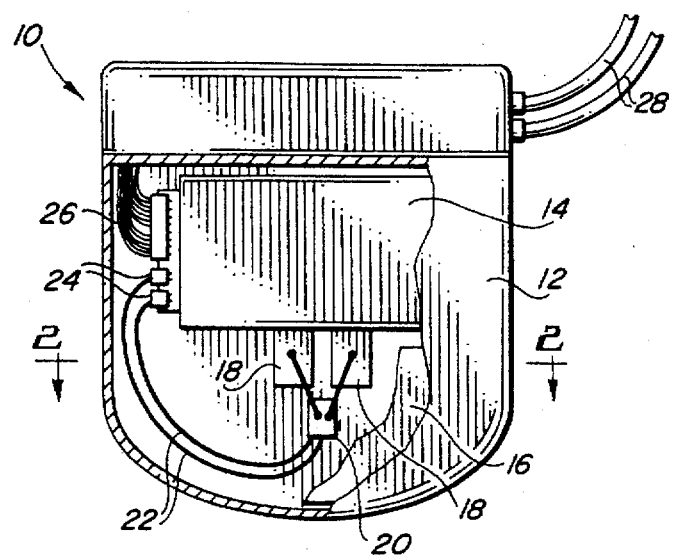
FIG. 1 is a plan cutaway view of the internal components of a pacemaker as seen in the prior art.

Referring initially to FIG. 1, an implantable pacemaker 10 is shown as found in the prior art. The pacemaker 10 has an exterior two-piece housing 12 which is shown in a partial cutaway view. Beneath the housing 12 are internal electrical components of the pacemaker which include an electronics package 14, and a battery 16 also shown in a partial cutaway view. An electronic motion detecting element, consisting of piezoelectric sensors 18 and a resistor board 20, is mounted underneath the electronics package 14 and the battery 16. Electronic signals from the sensors 18 are transmitted to the electronics package 14 for processing via wires 22 and connectors 24. Pacing information is sent from the electronics package 14 through wires 26 to provide an electronic stimulus to the heart of a patient. Stimulus leads 28 transmit the pacing information directly to the heart of a patient.

In the prior art embodiment shown in FIG. 1, the sensors 18 and the resistor board 20 both have a thin dimension and a relatively large amount of surface area. Accordingly, these elements are typically mounted beneath the battery or the electronics package as shown to minimize the size of the pacemaker. Although the sensors 18 and the board 20 are thin electronic components, their placement beneath the electronics package or the battery does contribute to an increased pacemaker size.

Figure 2:
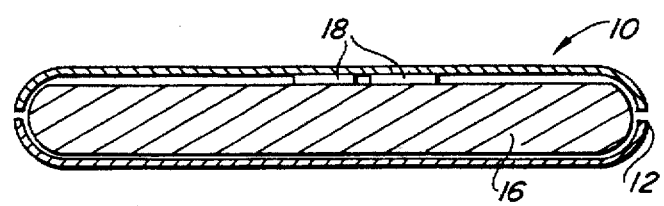
FIG. 2 is an elevation view of the pacemaker shown in FIG. 1 taken along the line 2—2.

FIG. 2 is an elevation view of the prior art pacemaker shown in FIG. 1. In FIG. 2, the sensors 18 are seen in their mounted position which adds to the overall width of the pacemaker 10. Accordingly, the housing 12 used in the prior art must be designed to accommodate this increased width of the pacemaker 10.

Figure 3:
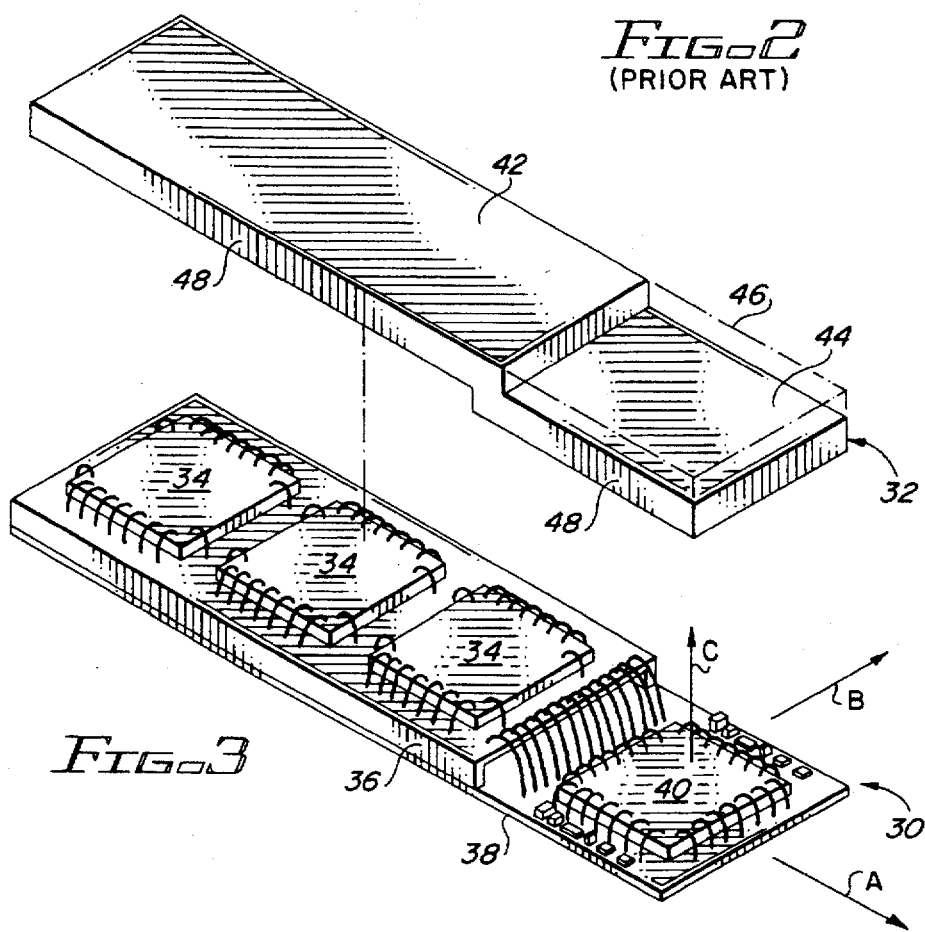
FIG. 3 is a perspective view of an electronics package and a contoured hybrid lid of a pacemaker constructed in accordance with a preferred embodiment.

FIG. 3 is a perspective view depicting an electronics package 30 having a contoured hybrid lid 32 in accordance with a preferred embodiment. The electronics package 30 is a hybrid circuit structure containing various integrated circuits which are vertically stacked at different positions to create a multi-level circuit structure. In particular, the package 30 contains a group of integrated circuits 34, which may be random access memory (RAM) chips, mounted atop a platform 36. Underneath the platform 36 are additional electronic components (not shown) which are mounted to a substrate 38 and which communicate with the integrated circuits 34. An additional integrated circuit 40 is mounted directly to the substrate 38 and is not covered by the platform 36. The dimensions of the electronics package 30 extend along a longitudinal direction A, extend to a width along a transverse direction B, and extend to a height along a lateral direction C.

Previous lids found in the prior art for covering an electronics package of a pacemaker employed a single-level rectangular structure. The height of such a structure was typically that needed to cover the tallest component of the electronics package. Use of such a single-level lid structure can create unused space within the electronics package if the underlying electronic components are of unequal height. This is especially true when the components of the electronics package are integrated circuits or some semiconductor component having a relatively larger size than individual passive circuit components.

The contoured lid 32 of the present invention is designed to conform to the multi-level circuit structure of the package 30. Specifically, the contoured lid 32 is formed with a cover surface having a first surface portion 42 for placement over the integrated circuits 34. The cover surface of the contoured lid 32 also has a second surface portion 44, which is offset with respect to the first portion 42, for placement over the integrated circuit 40. A series of connected support surfaces 48 form a perimeter about the surface portions 42 and 44 for attachment to the substrate 36. The first portion 42 and second portion 44 of the lid 32 are in different elevational planes whereby the second portion 44 is slightly recessed with respect to the first portion 42. In accordance with a preferred embodiment, use of the contoured lid 32 creates an isolated region 46 (shown in phantom) above the surface portion 44 which is exterior of the package 32. The isolated region 46 can thus be used in a manner not found in the prior art to house additional components of a pacemaker.

Electronics packages of pacemakers, like that shown in FIG. 3, must be designed to withstand temperature fluctuations which can occur during use. These temperature fluctuations have a small bending or warping effect on the substrate 38 and the lid 32. Accordingly, use of a contoured hybrid lid must be engineered to accommodate such bending. It has been found that use of ceramic material for constructing the contoured lid 32 provides adequate resiliency towards bending during temperature fluctuations of the package 30.

Figure 4A:
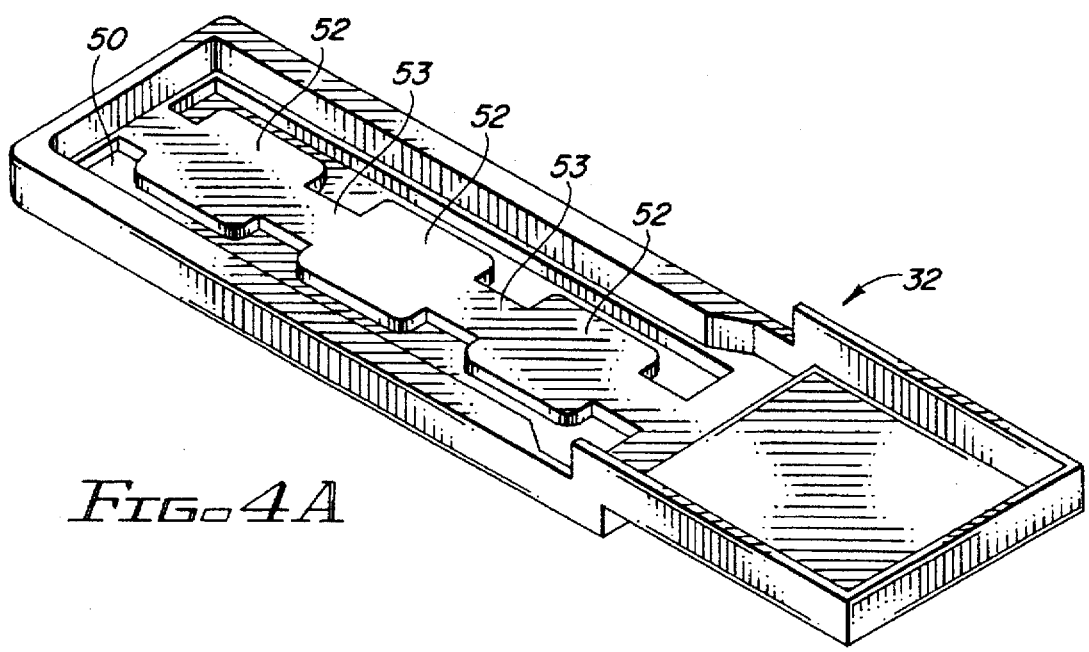
FIGS. 4A and 4B are perspective views of two embodiments for the inside of the contoured lid shown in FIG. 3.
Figure 4B:
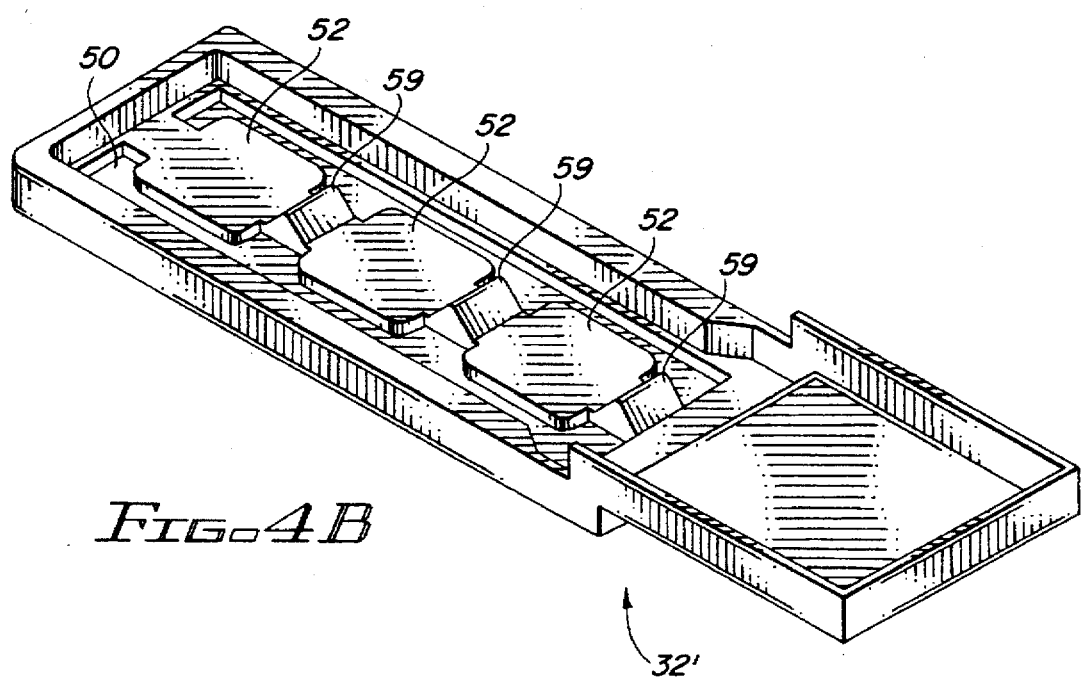

In addition to the external contour creating the surfaces 42 and 44, the contoured lid 32 can be constructed with additional internal contours to improve the strength of the lid 32. Referring to FIGS. 4A and 4B, two embodiments for the internal side of the contoured lid 32 are shown. In accordance with a preferred embodiment, the lid 32 has thicker portions 52 positioned above each of the integrated circuits 34. The thicker portions 52 are connected together with support structures 53 (or 59, as shown in FIG. 4B) to improve overall strength. Recessed, or thinner, portions 50 of the lid 32 accommodate wire bonds used to connect the integrated circuits 34 to the substrate 38 or other electronic components. The overall variable-thickness structure of the lid 32 serves to maximize space within the electronics package 30 while maintaining a sufficiently strong and durable lid 32.

Figure 5:
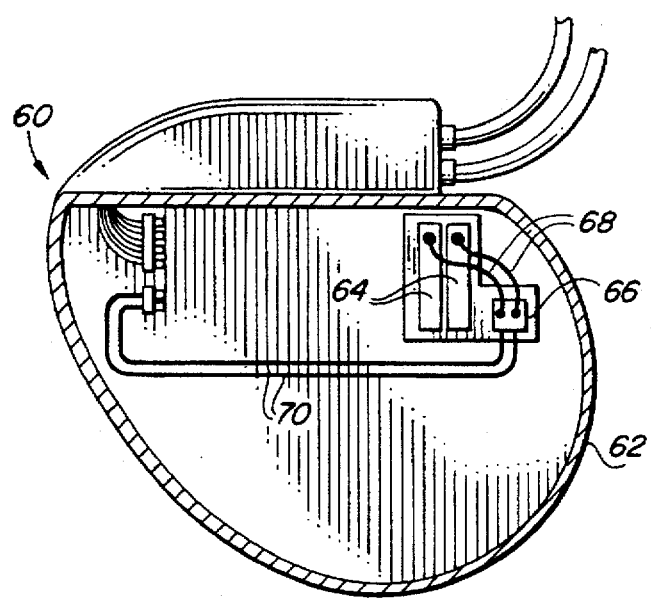
FIG. 5 is a plan view of a pacemaker housing having an electronic component mounted within an isolated region of a pacemaker housing.

FIG. 5 depicts an internal view of a partially disassembled pacemaker 60 in accordance with a preferred embodiment. The pacemaker 60 has a first segment 62 of a pacemaker housing within which are mounted piezoelectronic sensors 64 and a resistor board 66. The sensors communicate with the resistor board 66 via wires 68. The resistor board 68 in turn communicates with an electronics package (not shown) via wires 70. The sensors 64 and resistor board 66 are advantageously mounted, or attached, within the housing segment 62 to coincide with the isolated region 46 (shown in FIG. 3) created by the contoured lid 32.

Figure 6:
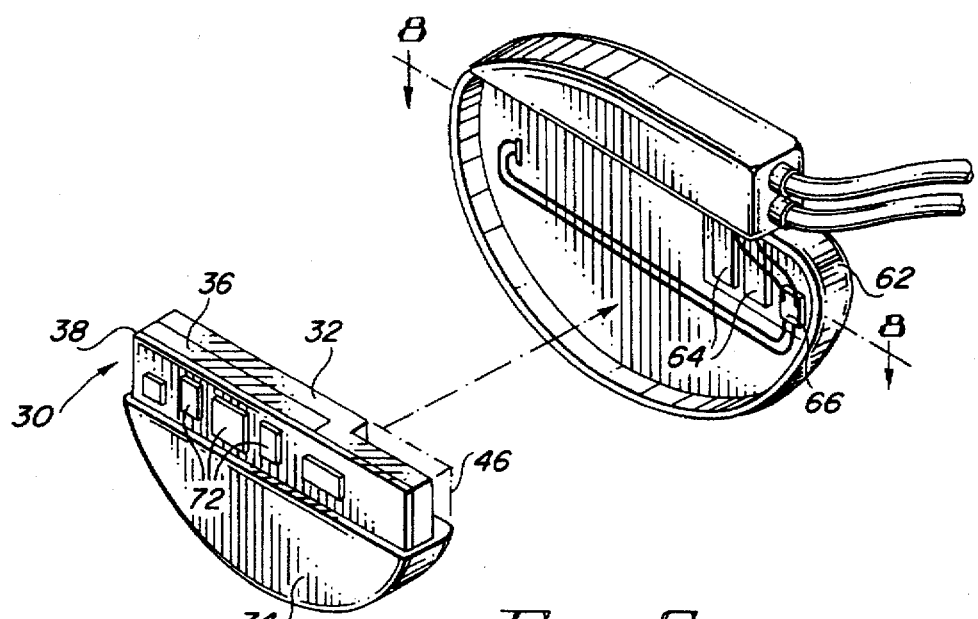
FIG. 6 is a perspective view of a preferred embodiment of the present invention showing the placement of the electronics package and the battery within the housing of the pacemaker.

FIG. 6 depicts the pacemaker 60 of FIG. 5 adapted to receive the electronics package 30 and a battery unit 74 of the pacemaker 60. As can be seen in FIG. 6, the isolated region 46 associated with the package 30 will accommodate the sensors 64 and the resistor board 66. Also, in a typical pacemaker, the electronics package 30 may contain electronic components 72 mounted to an underside of the substrate 38 as shown. The sensors 64 and board 66, or other electronic components, may be mounted to the housing segment 62, the lid 32 of the package 30, or they may be friction fitted within the isolated region 46 created by the contoured lid 32.

Figure 7:
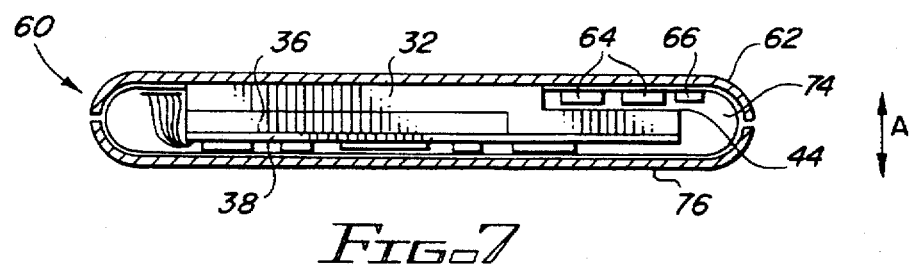
FIG. 7 is an elevation view of the pacemaker shown in FIG. 6 taken along the line 7—7.

FIG. 7 depicts the final configuration of the internal components of the pacemaker 60 as seen along the line 8—8 of FIG. 6. In accordance with a preferred embodiment, the activity sensor of a pacemaker consisting of components 64 and 66 is mounted in a previously unused internal region of a pacemaker. Specifically, the sensors 64 and the resistor board 66 are mounted between the exterior surface 44 of the lid 32 and an interior surface of the housing segment 62. A second segment 76 of the pacemaker housing is placed over the electronics package 30, the battery 74, and the remaining internal components of the pacemaker 60.

Creation of the internal region 46 which can accommodate pacemaker components leads to smaller overall pacemaker dimensions. In particular, the width of the pacemaker 60, denoted by the distance A in FIG. 7, is significantly reduced over that of prior art pacemaker units. This translates into a direct benefit for the patient who must carry the pacemaker 60. In addition, the smaller dimensions of the pacemaker 60 help improve the surgical procedures required to install such pacemakers within a patient.

Although the description and the figures above depict a piezoelectric activity sensor mounted within the region 46, an accelerometer or other activity-sensing element may be placed in the same region. In addition, any internal pacemaker element, electronic or otherwise, may possibly be placed within the region 46 to minimize the size of a pacemaker or other implantable medical device. Moreover, depending on the configuration of the circuitry mounted on the substrate 38, multiple isolated regions may be created with a contoured lid to conform to multiple heights of the associated circuitry. Finally, although the preceding description of a preferred embodiment has been demonstrated to be advantageous for pacemaker designs, the same principles can be applied for any implantable cardiac stimulation device such as a defibrillator or the like.

Through the foregoing description and accompanying drawings, the present invention has been shown to have important advantages over current apparatus and methods for configuring the internal components of a cardiac stimulation device. While the above detailed description has shown, described, and pointed out the fundamental novel features of the invention, it will be understood that various omissions, substitutions and changes in the form and details of the device and methods illustrated may be made by those skilled in the art, without departing from the spirit of the invention. Therefore, the invention should be limited in its scope only by the following claims.

What is claimed is:

1. In an implantable cardiac stimulation device of the type having pulse generating means, a housing and a first electronic component mounted on the housing, an electronics package for packaging the pulse generating means, said electronics package comprising:

a substrate for mounting electronic components on a surface of the substrate;

a second electronic component situated on the surface of the substrate, the second electronic component extending a first distance above the surface of the substrate;

a third electronic component situated on the surface of the substrate, the third electronic component extending a second distance above the surface of the substrate; and a contoured lid attached to the substrate and having a cover surface adapted to fit over the first and second electronic components, the cover surface having a first portion placed over the first component and a second portion placed over the second component, wherein the first and the second portions are offset to provide a multi-level contoured lid;

wherein, when the electronics package is placed within the housing, the first electronic component is adapted to fit within an isolated region which is formed between an exterior portion of the contoured lid and an interior surface of the housing.

2. The electronics package of claim 1, wherein the second electronic component is a single integrated circuit and the third electronic component comprises a platform having a first plurality of integrated circuits mounted thereon, the third electronic component enabling a second plurality of electronic components to be mounted on the substrate beneath the platform.

3. The electronics package of claim 1, wherein the contoured lid is formed with interior support structures for strengthening the contoured lid.

4. The electronics package of claim 1, wherein the first electronic component is a piezoelectric activity sensor.

5. The electronics package of claim 1, wherein the contoured lid is made of ceramic material.

6. A cardiac stimulation device comprising:

pulse generating means for generating stimulation pulses to a patient's heart, the pulse generating means including a plurality of electronic components having different elevational levels;

a hybrid circuit assembly having means for mounting the plurality of electronic components upon a substrate surface;

a lid placed over the electronic components and attached to the substrate surface for confining the electronic components, the lid having a contoured surface forming a plurality of elevational levels corresponding to the elevational levels of the plurality of electronic components;

a housing for receiving the hybrid circuit assembly and attached lid such that an isolated region is formed within the housing between the contoured surface of the lid and an interior of the housing; and sensor means, located within the isolated region and electrically coupled to the pulse generating means, for adjusting the rate of stimulation pulses.

7. The cardiac stimulation device of claim 6, wherein the sensor means is a patient activity sensor for sensing metabolic need.

8. The cardiac stimulation device of claim 6, wherein the plurality of electronic components comprises a first integrated circuit mounted at a first elevational level above the substrate surface and a second integrated circuit mounted at a second elevational level above the substrate surface.

9. The cardiac stimulation device of claim 6, wherein the lid is formed with interior support structures.

10. The cardiac stimulation device of claim 6, wherein the lid has a variable thickness corresponding to the placement of the plurality of electronic components upon the substrate surface.

11. The cardiac stimulation device of claim 6, wherein the lid is ceramic.

12. A method of creating a confined region within a pacemaker housing for mounting a component of the pacemaker comprises the following steps:

mounting the component of the pacemaker to an interior surface of the pacemaker housing;

constructing an electronics package having a circuit assembly covered by an associated lid, the lid having a contoured surface corresponding to a multi-level circuit structure of the circuit assembly; and placing the electronics package within the pacemaker housing such that a recessed portion of the contoured lid surface forms an isolated region within the housing to receive the component mounted to the pacemaker housing, thereby creating the confined region between the contoured surface of the lid and the interior surface of the pacemaker housing.

13. A method of configuring the internal components of a pacemaker within a housing of the pacemaker wherein the internal components comprise a hybrid circuit assembly and at least one other individual component, the method of configuring comprising the following steps:

forming a contoured lid having a plurality of surface elevations corresponding to a plurality of elevations created by placement of circuit components within the hybrid circuit assembly;

placing the contoured lid over the hybrid circuit assembly to form an electronics package;

placing the electronics package within the housing of the pacemaker to create at least one isolated region between an exterior surface of the contoured lid and an interior surface of the pacemaker housing; and mounting the at least one other individual component within the at least one isolated region within the pacemaker housing.

14. The method of claim 13, wherein the at least one other individual component is an activity sensor for detecting movement of a patient when the pacemaker is implanted within the patient.

15. The method of claim 13, wherein the contoured lid is made of ceramic material.

* * * * *